United States Patent [19]
Tomizuka et al.

[11] Patent Number: 5,518,527
[45] Date of Patent: May 21, 1996

[54] METHOD FOR RECOVERING ETHYLENE FROM VENT GAS FROM ETHYLENE OXIDE PLANT VENT GAS

[75] Inventors: Yasuhiro Tomizuka; Yoshihiro Saitou, both of Kashima; Kiyoshi Itoga, Kawanishi; Masanori Tsuji, Akashi, all of Japan

[73] Assignees: Mitsubishi PetroChemical Engineering Co., Ltd., Tokyo; Takeda Chemical Industries, Ltd., Osaka, both of Japan

[21] Appl. No.: 290,119

[22] Filed: Aug. 15, 1994

[30] Foreign Application Priority Data

Aug. 26, 1993 [JP] Japan ................... 5-211291

[51] Int. Cl.⁶ ...................... B01D 53/047
[52] U.S. Cl. ................ 95/101; 95/104; 95/144; 95/903
[58] Field of Search ............. 95/96–98, 100–105, 95/139, 143, 144, 903

[56] References Cited

U.S. PATENT DOCUMENTS

| | | | |
|---|---|---|---|
| 2,635,709 | 4/1953 | Archibald et al. | 95/144 |
| 3,388,532 | 6/1968 | Kunugi et al. | 95/144 |
| 3,458,973 | 8/1969 | Spencer et al. | 95/144 |
| 4,256,773 | 3/1981 | Itoga et al. | 95/144 X |
| 4,261,709 | 4/1981 | Itoga et al. | 95/144 X |
| 4,498,910 | 2/1985 | Benkmann | 95/144 X |
| 4,529,415 | 7/1985 | Szirmay | 95/144 |
| 4,554,141 | 11/1985 | Scull et al. | 95/144 |
| 4,599,094 | 7/1986 | Werner et al. | 95/101 |
| 4,627,857 | 12/1986 | Sutt, Jr. | 95/144 X |
| 4,629,476 | 12/1986 | Sutt, Jr. | 95/144 X |
| 4,769,047 | 9/1988 | Dye | 95/144 X |
| 4,775,394 | 10/1988 | Yamano et al. | 95/101 |
| 4,790,859 | 12/1988 | Marumo et al. | 95/903 X |
| 4,857,083 | 8/1989 | DiMartino | 95/101 X |
| 4,933,314 | 6/1990 | Marumo et al. | 95/903 X |
| 5,104,425 | 4/1992 | Rao et al. | 95/144 X |
| 5,176,722 | 1/1993 | Lemcoff et al. | 95/102 |
| 5,206,004 | 4/1993 | Park | 95/144 X |
| 5,245,099 | 9/1993 | Mitariten | 95/144 X |

FOREIGN PATENT DOCUMENTS

| | | | |
|---|---|---|---|
| 0294036 | 12/1988 | European Pat. Off. | 95/144 |
| 63-116721 | 5/1988 | Japan | 95/144 |

*Primary Examiner*—Robert Spitzer
*Attorney, Agent, or Firm*—Armstrong, Westerman, Hattori, McLeland & Naughton

[57] ABSTRACT

The present invention provides a method for economical recovery of ethylene from ethylene-containing vent gas from a plant for production of ethylene oxide, wherein ethylene is separated from saturated hydrocarbons such as methane, ethane and oxygen and then recovered efficiently. In this method, the vent gas is made to contact with molecular sieve carbon to selectively adsorb ethylene without substantial adsorption of the oxygen contained in the vent gas, the ethylene then being desorbed and recovered.

7 Claims, 1 Drawing Sheet

METHOD FOR RECOVERING ETHYLENE FROM VENT GAS FROM ETHYLENE OXIDE PLANT VENT GAS

BACKGROUND OF THE INVENTION

1. Field of the Invention

The present invention relates to a method for recovering ethylene from vent gas from a plant for production of ethylene oxide. More specifically, the present invention relates to a method for separating ethylene from saturated hydrocarbon such as methane, ethane and oxygen contained in the vent gas, by which the ethylene can be recovered efficiently.

2. Description of the Prior Art

In the plants for producing ethylene oxide by oxidation of ethylene, the process gas obtained after recovering ethylene oxide from the effluent reaction gas contains a large amount of unreacted ethylene. Therefore, the process gas is recirculated back into the reaction system in order to enhance the reaction efficiency of ethylene.

The process gas also contains, besides the unreacted ethylene, saturated hydrocarbons such as methane and ethane, inert gases such as carbon dioxide, argon and nitrogen and oxygen. As a result of the repeated circulation of the gas into the reaction system, the inert gases, such as nitrogen and argon, are concentrated, and a part of the concentrates are continuously withdrawn out of the reaction system to be utilized as fuel gas.

The vent gas, however, usually contains about 30% ethylene, and it is uneconomical to use the gas only as fuel gas. Therefore, in order to re-use the gas as raw material gas, various methods for recovering ethylene from the vent gas have been proposed wherein the vent gas is treated with silica gel or active carbon to adsorb the ethylene and then desorbing and recovering the ethylene therefrom (see, for example, Japanese Patent Application Laid-open Nos. 109117/1983, 174732/1985 and 116721/1988).

However, these methods have the following disadvantages:

(i) As even methane, contained in the vent gas in a larger amount than ethylene, is adsorbed as well as ethylene, the amount of gas recovered by means of desorption is increased. Generally, in the re-circulation to the ethylene oxide-production plant, the recovered gas must be repressurized to the reaction pressure (normally 20 kg/cm$^2$). From the industrial viewpoint, it is greatly uneconomical to pressurize the gas accompanying methane which is inert for the oxidation reaction.

(ii) The complete separation and removal of inert gases (e.g. argon, nitrogen, carbonic acid gas, etc.) contained in the vent gas surely causes loss of ethylene into the exhaust gas; whereas, the improvement of recovery efficiency of ethylene results in an increase in concentration of the inert gases such as argon in the recovered gas; which is not desirable.

Accordingly, it is difficult for such conventional methods to avoid the loss of ethylene and give the recovered gas containing ethylene in a high concentration efficiently.

SUMMARY OF THE INVENTION

The object of the present invention is to solve the problems of the conventional methods described above and to provide a method for recovering ethylene from vent gas efficiently.

The present inventors have carried out extensive studies to solve the problems above. As the result, they have found that the use of specially designed molecular sieve carbon enables ethylene to be efficiently separated from saturated hydrocarbon gas such as methane, ethane and oxygen contained in the vent gas from a plant for producing ethylene oxide, and this finding led to the present invention.

That is, the present invention relates to a method for recovering ethylene from a vent gas mixture from a plant for production of ethylene oxide by oxidation of ethylene, which is characterized in that the ethylene-containing vent gas is made to contact with a molecular sieve carbon under pressure to selectively adsorb the ethylene, the ethylene being then desorbed under reduced pressure and recovered.

DETAILED DESCRIPTION OF THE INVENTION

Figure 1:
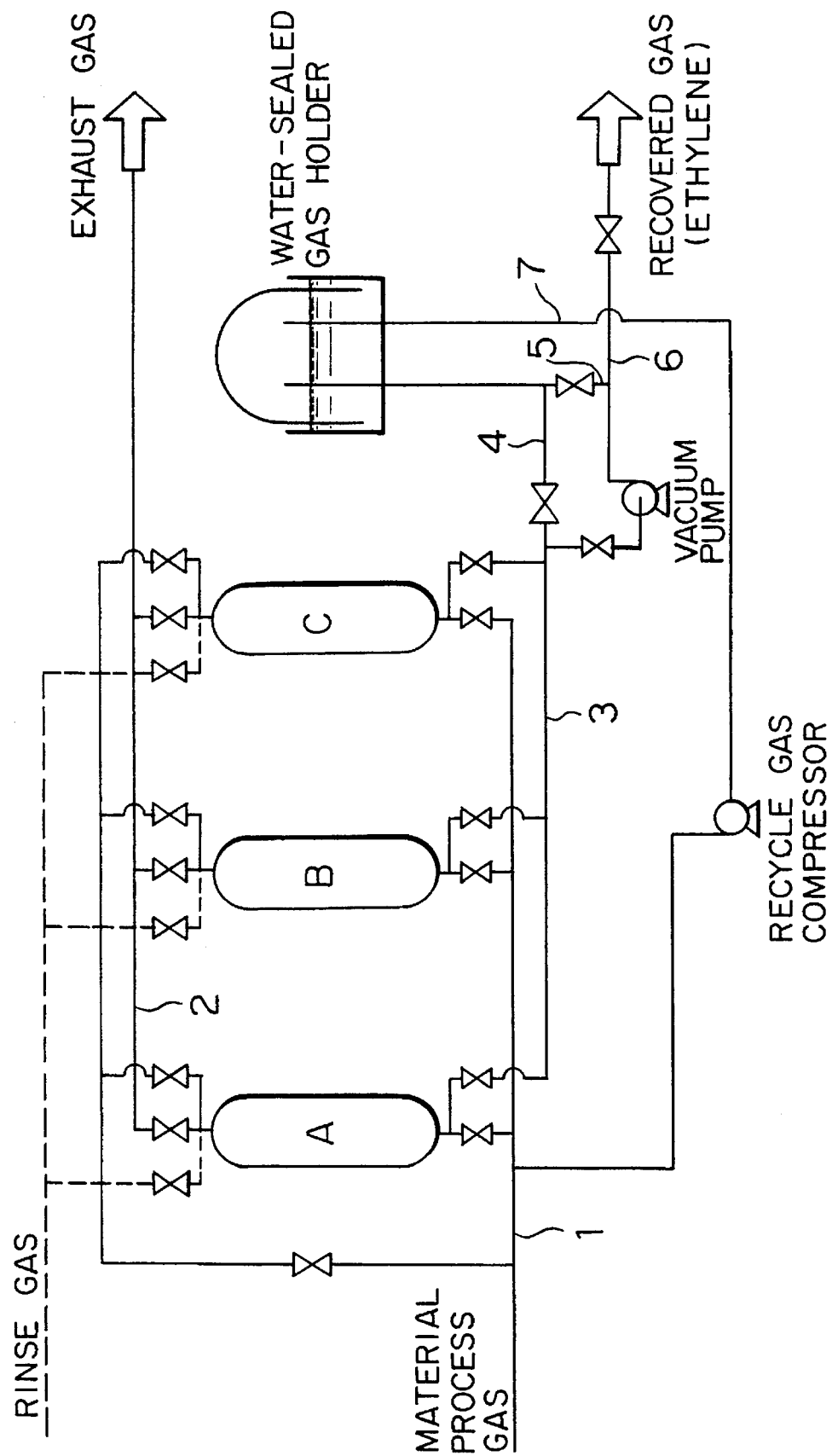
FIG. 1 schematically illustrates an embodiment of the process flow according to the present invention.

In the present invention, vent gas (referred to as "process gas", hereinafter) from a plant for production of ethylene oxide by oxidation of ethylene is at first made to contact with molecular sieve carbon under pressure (referred to as "adsorption step", hereinafter).

The molecular sieve carbon to be used in the present invention (also termed "carbon molecular sieve", "molecular sieving carbon", "molecular sieving active carbon" and so on) is composed of microcrystalline carbon similar to active carbon, and therefore its properties (e.g. elemental composition, chemical properties, adsorption selectivity to polar molecules, etc.) are almost similar to those of active carbon. However, the molecular sieve carbon to be used in the present invention has uniform ultramicropores of not more than 10 Å in diameter therein, and also exhibits molecular sieving properties.

Molecular sieve carbon can be manufactured, for example, according to the method disclosed in Japanese Patent Publication No. 18675/1977. That is, coke having a volatile material content of up to 5%, is added to a hydrocarbon which can release carbon by thermal decomposition and then treated with heat at 600° to 900° C. for 1 to 60 min., whereby the carbon released comes to partially pack the micropores of the coke, thus forming the molecular sieve carbon made of coke. Molecular sieve carbons can also be manufactured according to the methods disclosed in Japanese Patent Publication No. 37036/1974, Japanese Patent Application Laid-open No. 45914/1984, and so on.

As the molecular sieve carbons to be used in the present invention, preferably employed are those having the following physical properties:

(i) Mean micropore diameter: 3 to 5 Å;

(ii) Equilibrium adsorption rate (at 25° C. under 1 atm.):

The equilibrium adsorption rates for each compound are as follows:

ethylene: 35 to 65 Nl/kg, preferably 40 to 60 Nl/kg ethane: 35 to 65 Nl/kg, preferably 40 to 60 Nl/kg carbon dioxide: 25 to 60 Nl/kg, preferably 30 to 55 Nl/kg methane: 10 to 30 Nl/kg, preferably 15 to 25 Nl/kg (iii) Adsorption parameter:

The term "adsorption parameter" used here means a value determined as the time required for adsorption of each compound in a half amount of its equilibrium adsorption rate. The adsorption parameter for each compound at 25° C. under 1 atm is as follows:

ethylene: 0.2 to 10 min., preferably 0.3 to 5 min., especially preferably 0.4 to 4 min.

ethane: 40 to 3000 min., preferably 60 to 2000 min. especially preferably 80 to 1500 min.

carbon dioxide: 0.01 to 0.3 min., preferably 0.015 to 0.2 min., especially preferably 0.02 to 0.15 min.

methane: 1 to 200 min., preferably 2 to 100 min., especially preferably 3 to 60 min.

A molecular sieve carbon having these physical properties can be manufactured according to the methods described above by properly selecting the conditions thereof.

In the present invention, various forms of molecular sieve carbon can be employed, such as pellet form, crushed form and a honeycomb form molding. Among these, the pellet form of molecular sieve carbon is preferable. The granule size of the molecular sieve carbon is preferably not more than 3 mmφ, and more preferably not more than 2 mmφ. However, too small of a granule size is not industrially preferable, since it may cause a larger loss in pressure.

The process gas described above usually contains about 15 to about 35% by volume ethylene and about 45 to about 65% by volume of methane, and in addition about 1 to about 8% by volume of each of carbon dioxide, oxygen and argon and 1% by volume or less of ethane.

The adsorption treatment is carried out under pressure, and preferably under a pressure of about 5 to about 20 $kg/cm^2$ in general. As the pressure of vent gas formed in the ethylene oxide plant is generally 13 to 17 $kg/cm^2G$, it is economical to carry out the adsorption treatment under a pressure within this range.

The adsorption time in the adsorption step is 6 to 10 min. and preferably 7 to 8 min. In this case, the flow rate of the feed gas is suitably about 40 to about 120 times the volume of adsorbent in column (SV=40–120/hr). A flow rate of about 50 times gives high ethylene recovery.

The temperature to be employed during the adsorption is initially ordinary temperature, for example about 20° to about 50° C. Although the temperature raises gradually due to the heat generated by the adsorption reaction, control of temperature is not particularly necessary.

The present invention will be illustrated in detail with reference to the drawing as follows.

FIG. 1 illustrates an embodiment of the process flow of the method according to the present invention.

In the method of FIG. 1, three adsorption towers A, B and C are applied. However, the number of towers can be increased, if necessary. Into each adsorption tower, molecular sieve carbon is charged as an adsorbent.

The process gas, i.e. the vent gas containing ethylene, is fed into tower A through gas supply line 1, and then is caused to contact with the adsorbent in the tower, by which ethylene and carbon dioxide are mainly adsorbed onto the adsorbent. In this adsorption step, most of the ethylene contained in the vent gas can be adsorbed, for example by more than 90%. Although oxygen is also adsorbed in part, the amount adsorbed is less than 1%.

The gas thus withdrawn from the adsorption tower contains only a trace amount of ethylene (less than 5%) and is mainly composed of methane, which is withdrawn from exhaust line 2 placed over the adsorption tower.

Next, in adsorption tower A, desorption of ethylene from the adsorbent is carried out. On the other hand, during the desorption process in adsorption tower A, the process gas is newly supplied into adsorption tower C, where the same adsorption procedures as described above are carried out. In the desorption step, as the adsorption tower has normally been rendered into a pressurized state, the gas components adsorbed onto the adsorbent are desorbed until the tower is depressurized to ambient pressure.

When the internal pressure of the adsorption tower reaches ordinary pressure, the adsorption tower is subsequently vacuumed by means of a suction pump, e.g. a vacuum pump, to reduce the internal pressure to about 50 to about 500 Torr, whereby the gas components adsorbed can be sufficiently desorbed. The temperature required for the desorption varies depending on the desorption speed and the amount of the components desorbed, but generally is within the range of about −5° C. to about 30° C.

In the initial stage of the desorption step, the concentration of ethylene contained in the effluent gas from the adsorption tower is very low. Therefore, the effluent gas is initially fed into the gas holder through the effluent lines 3 and 4 or 5, and then switched to the line 6 and recovered when the effluent gas enriched with ethylene begins to be evacuated.

Otherwise, as another method, during the initial stage of the desorption caused by the residual pressure of the tower, after withdrawing the adsorbed gas with less ethylene content from the exhaust line 2 via the top of the adsorption tower, the gas enriched with ethylene may be desorbed and recovered from the effluent line 3 via the bottom of the adsorption tower.

For more complete desorption, rinse gas can be introduced from the top of the adsorption tower. The rinse gas to be used contains substantially no oxygen and is mainly composed of methane, in order to prevent the oxygen concentration in the recovered gas from shifting to the flammable limit.

The recovered gas thus obtained contains substantially no oxygen or ethane, and is mainly composed of ethylene with a minor amount of methane and carbon dioxide. Accordingly, the recovered gas can be re-used as a raw material gas for production of ethylene oxide.

On the other hand, the gas collected in the gas holder, of which the ethylene concentration is very low, is small in volume. Therefore, the gas may be fed back to the suction port side of the existing gas compressor for an ethylene oxide plant, or may be fed through line 7 into a recycle gas compressor, where the gas is repressurized and fed back to the supply line 1 for the raw material gas (i.e. process gas).

When the desorption step is complete, the adsorption tower A is then subjected to repressurization as a preparation step for the next adsorption. In this step, it is preferable to use a part of the process gas as a repressurizing agent for the purpose of preventing a dangerous shifting to the flammable limit.

EXAMPLES

The following examples are given for the purpose of more fully illustrating the present invention.

EXAMPLE 1

In this expample, as shown in FIG. 1, a system with three adsorption towers were employed. The desorption towers all had similar structures and were charged with molecular sieve carbon ("Molsievon HGY-813"; a trade name produced by Takeda Chemical Industries, Ltd.) as an adsorbent. The physical properties of the molecular sieve carbon used were as follows:

Mean micropore size: 4.2 Å;
Equilibrium adsorption rate:
ethylene: 47.5 Nl/kg,
ethane: 49.0 Nl/kg,
carbon dioxide: 40.1 Nl/kg,
methane: 20.3 Nl/kg;
Adsorption parameter:
ethylene: 0.65 min.,
ethane: 190 min.,
carbon dioxide: 0.038 min.,
methane: 6.4 min.

As process gas, a mixed gas of the composition shown in the left column of Table 1 was used, which was a make-up gas of the vent gas withdrawn from an ethylene oxide plant.

<Adsorption step>

The process gas was fed into the bottom part of the adsorption tower A through the supply tube 1 at 20° C. under a pressure of 7 kg/cm$^2$G at a flow rate of about 0.31 m$^3$/hr (SV=50), then made to fully contact with the adsorbent, and subsequently withdrawn from the exhaust tube 2 out of the tower (exhaust speed: 0.16 m$^3$/hr, treating time: 8 min.). As a result, the exhaust gas having the composition shown in the middle column of Table 1 was obtained.

<Desorption step>

In this step, the pressure inside of the adsorption tower was released, by which the gas adsorbed came to flow out of the tower through the effluent line 3 by the aid of residual pressure. The tower was evacuated by means of a vacuum pump to 100 Torr to recover the desorbed gas. At this point of time, the temperature of the bottom part of the adsorption layer was 3° C. The recovered gas thus obtained had the composition shown in the right column of Table 1. In this process, the recovery rate of ethylene was 90%.

<Repressurization step>

In order to proceed to the next adsorption step, a part of the process gas was newly supplied into the adsorption tower from the top part thereof, by which the pressure inside of the tower was elevated to 7 kg/cm$^2$G.

TABLE 1

| Component | Gas composition (% by vol.) | | |
|---|---|---|---|
| | Process gas | Exhaust gas | Recovered gas |
| Ethylene | 30.0 | 4.8 | 73.0 |
| Carbon dioxide | 6.0 | 1.6 | 13.5 |
| Methane | 52.0 | 75.7 | 13.5 |
| Oxygen | 6.0 | 9.7 | <1 |
| Ethane | <1 | <1 | — |
| Nitrogen | <1 | <1 | — |
| Argon | 5.0 | 5.0 | — |

According to the procedures described above, the adsorption step, desorption step and repressurization step are carried out in succession in the three adsorption towers. The sequences for the operation carried out in the individual towers are as follows:

Adsorption tower A: Adsorption—Desorption—Repressurization

Adsorption tower B: Desorption—Repressurization—Adsorption

Adsorption tower C: Repressurization—Adsorption—Desorption

As described above, the method of the present invention allows the efficient recovery of gas enriched with ethylene, for example, having an ethylene content of 65 to 75% by volume, which contains substantially no oxygen or, if any, extremely small amounts of oxygen, from the vent gas from an ethylene oxide plant. In addition, the method also allows almost the complete removal of ethane and so on from the gas recovered. Therefore, the method is safe for re-using the recovered gas and extremely suitable for industrial applications.

What is claimed is:

1. A method for recovering ethylene from vent gas from a plant for production of ethylene oxide by oxidation of ethylene, comprising the steps of:

contacting vent gas comprising about 15% by volume ethylene or more with a molecular sieve carbon under pressure of about 5 to about 20 kg/cm$^2$, wherein the molecular sieve carbon has an equilibrium adsorption rate for ethylene of about 35 to 65 Nl/kg at 25° C. under 1 atm and selectively adsorbing ethylene contained in the vent gas to the molecular sieve carbon, desorbing the ethylene under reduced pressure of about 50 to about 500 Torr, and recovering ethylene.

2. The method of claim 1, wherein the molecular sieve carbon has a mean micropore diameter of 3 to 5 Å and an adsorption time required for adsorption of half of the equilibrium adsorption amount of ethylene and ethane of 0.2 to 10 min., and 40 to 3000 min., respectively, at 25° C. under 1 atm.

3. The method according to claim 1, wherein the molecular sieve carbon has adsorption parameters for carbon dioxide and methane of 0.01 to 0.3 min. and 1 to 200 min., respectively, at 25° C. under 1 atm.

4. The method according to claim 1, wherein the molecular sieve carbon has an equilibrium adsorption rate for ethane of about 35 to 65 Nl/kg, at 25° C. under 1 atm.

5. The method according to claim 1, wherein the vent gas contains about 15 to about 35% by volume ethylene and about 45 to about 65% by volume of methane, and in addition about 1 to about 8% by volume of each of carbon dioxide, oxygen and argon, and 1% by volume or less of ethane.

6. The method of claim 1, wherein the adsorbing step is performed at a temperature of about 20° to about 50° C.

7. The method of claim 1, wherein the desorbing step is performed at a temperature of about −5° to about 30° C.

\* \* \* \* \*